(12) United States Patent
Lukac et al.

(10) Patent No.: US 6,733,690 B1
(45) Date of Patent: May 11, 2004

(54) LATERALLY SUBSTITUTED CURABLE LIQUID CRYSTALS

(75) Inventors: Teodor Lukac, Basel (CH); Carsten Benecke, Weil am Rhein (DE); Richard Buchecker, Zürich (CH)

(73) Assignee: Rolic AG, Zug (CH)

( * ) Notice: Subject to any disclaimer, the term of this patent is extended or adjusted under 35 U.S.C. 154(b) by 0 days.

(21) Appl. No.: 09/936,725

(22) PCT Filed: Feb. 15, 2000

(86) PCT No.: PCT/IB00/00158

§ 371 (c)(1),
(2), (4) Date: Sep. 17, 2001

(87) PCT Pub. No.: WO00/55110

PCT Pub. Date: Sep. 21, 2000

(30) Foreign Application Priority Data

Mar. 17, 1999 (GB) .............................................. 9906168

(51) Int. Cl.$^7$ .............................................. C09K 19/20
(52) U.S. Cl. .......................... 252/299.67; 252/299.01; 252/299.61; 252/299.63; 560/61; 560/85
(58) Field of Search ....................... 252/299.01, 299.61, 252/299.63, 299.67; 560/61, 85

(56) References Cited

U.S. PATENT DOCUMENTS

| 5,164,111 A | * | 11/1992 | Dorsch et al. | .......... 252/299.01 |
| 5,593,617 A | * | 1/1997 | Kelly et al. | ............ 252/299.01 |
| 5,707,544 A | | 1/1998 | Kelly | |
| 6,319,963 B1 | * | 11/2001 | Coates et al. | ................ 428/1.1 |

FOREIGN PATENT DOCUMENTS

| EP | 0 748 852 | 12/1996 |
| WO | WO 99/37735 | 7/1999 |
| WO | WO 99/64924 | 12/1999 |
| WO | WO 00/04110 | 1/2000 |

* cited by examiner

*Primary Examiner*—Mark F. Huff
*Assistant Examiner*—Jennifer R Sadula
(74) *Attorney, Agent, or Firm*—Finnegan, Henderson, Farabow, Garrett, & Dunner, L.L.P.

(57) ABSTRACT

In one embodiment, the invention relates to compounds of the formula (I)

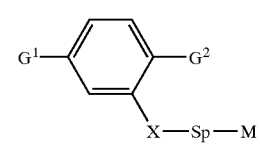

I wherein $G^1$ and $G^2$ independently represent a polymerisable mesogenic residue, X and Sp are as defined herein and M represents an achiral group of formula (II)

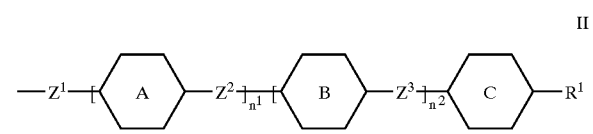

II as defined herein. The compounds of the invention may, for example, be useful as curable liquid crystals and for preparing liquid crystal films.

21 Claims, No Drawings

LATERALLY SUBSTITUTED CURABLE LIQUID CRYSTALS

This application is a national stage filing under 35 U.S.C. §371 of international application no. PCT/IB00/00158, filed on Feb. 15, 2000, which published in the English language. This application also claims the benefit of priority under 35 U.S.C. §119(a) to GB patent application no. 9906168.1, filed on Mar. 17, 1999.

The present invention relates to laterally substituted curable Liquid Crystals (LCPs) having mesogenic properties or properties which cause these LCPs to be compatible with a mesogenic molecular structure. In particular the present invention relates to laterally substituted curable Liquid Crystals (LCPs) with adjustable optical anisotropy and in parallel with low melting point or good supercoolability, relatively high clearing point and good alignment properties and the use of such LCPs in the preparation of substantially uniform or patterned film in which the orientation of the LCP molecules in the plane and relative to the plane of the substrate can be controlled.

Films prepared from curable Liquid Crystals (LCP films) are well known to a skilled person and are used in the preparation of optical and electro-optical devices. U.S. Pat. No. 5,650,534 discloses compounds and mixtures used to prepare components suitable for use non-linear optical (NLO) applications. These compounds are optically active and exhibit chiral smectic or chiral nematic mesophases. U.S. Pat. No. 5,707,544 also discloses compounds and mixtures suitable for use in NLO applications. However, these compounds are characterised by relatively high melting points. U.S. Pat. No. 5,593,617 discloses photochemically polymerisable liquid crystal compounds and mixtures, which are used to prepare optical and electronic components. However, these mixtures have a relatively narrow operating range and are unsuitable for use at higher temperatures.

LCP films are generally manufactured by using known coating techniques such as spin coating. This involves casting an organic solution of a cross-linkable LCP or LCP mixture onto a substrate provided with an orientation layer. The organic solvent is subsequently removed to give a well-oriented, solvent-free mesogenic LCP layer, which in turn is cross-linked to give an LCP film. The desired optical performance of such films depends crucially on some reproducible physical parameters which the LCP material has to fulfill simultaneously. Such properties are a nematic mesophase, a high clearing point, a low melting point or a low tendency to crystallise when cooled below melting point (supercooling), good solubility in organic solvents, good miscibility with other LCPs, good aligning properties on orientation layers, and the ability to form an adjustable tilt out of the substrate plane essentially free of tilt domains and disclinations. Tilt domains are regions within the LCP film in which the long axes of the LCP molecules form tilt angles out of the plane of the substrate of the same size but in opposite direction. Disclinations are borderlines of neighbouring tilt domains where LCP molecules of opposite tilt angles are adjacent. These tilt domains and disclinations result in both a disturbance in the uniform appearance of the film and an inhomogeneous optical performance.

Good aligning properties and the ability to form an adjustable tilt angle are of particular relevance if photo-orientated and photo-patterned orientation layers are used for the orientation of LCPs. This so-called linear photo-polymerisation (LPP) technology (cf. e.g. *Nature*, 381, p. 212 (1996)) allows the production of not only uniform but also structured (photo-patterned) orientation layers. If such structured orientation layers are used for the orientation of LCPs, the LCP molecules should adapt the information given by the orientation layer with respect to the direction of alignment and the tilt angle.

For adjusting the optical properties of the layers and films prepared from LCPs as for example retardation films, it is further essential to have available a variety of LCP materials with differing optical anisotropy, mainly high optical anisotropy. It is known that LCPs exhibiting a high optical anisotropy often show a negative impact on several of the above properties. Particularly the formation of smectic mesophases, high melting points, an enhanced tendency to crystallise, a low solubility in organic solvents or reduced miscibility with other LCPs is observed. Furthermore the ability of homogeneous alignment free of tilt domains and disclinations is often reduced.

There is, therefore, a need for a new LCP material that may be used in the preparation of an LCP mixture, which significantly reduces the aforementioned disadvantages. The present invention addresses that need.

A first aspect of the invention provides a compound of formula (I)

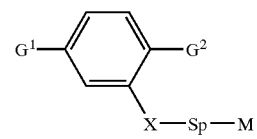

I wherein $G^1$ and $G^2$ independently represent a polymerisable mesogenic residue;

X represents a group selected from —$CH_2$—, —O—, —CO—, —COO—, —OOC—, —CONR'—, —OCOO—, —OCONR';

Sp represents a group of the formula —$(CH_2)_p$— in which p is an integer of 1 to 18 and in which one or two non adjacent —$CH_2$— groups are optionally replaced by —CH=CH—; or in which one or two —$CH_2$— groups are optionally replaced by one or two groups selected from the group consisting of —O—, —CO—, —COO—, —OOC—, —CONR'—, —OCOO—, —OCONR' with the proviso that firstly the spacer group does not contain two adjacent heteroatoms and secondly when X is —$CH_2$—, p can also have a value of 0; and M represents an achiral group of formula (II)

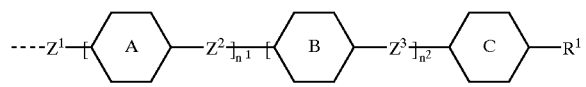

in which

A and B independently represent a six membered isocyclic or heterocyclic group or naphthalenediyl;

C is selected from the group consisting of a five and six membered isocyclic or heterocyclic group or naphthalenediyl;

$n^1$ and $n^2$ are 0 or 1 with the proviso that firstly $1 \leq n^1+n^2 \leq 2$ and secondly, when C is naphthalenediyl $0 \leq n^1+n^2 \leq 2$;

$Z^1$ is selected from the group consisting of —O—, —COO—, —OOC—, —CO—, —CONR'—, —NR'CO—, OCOO—, —OCONR'—, —NR'COO— and a single bond;

in which

R' is selected from the group consisting of hydrogen, a lower achiral alkyl group and a lower achiral alkenyl group;

$Z^2$ and $Z^3$ are independently selected from the group consisting of single bond, —COO—, —OOC—, —CH$_2$—CH$_2$—, —CH$_2$O—, —OCH$_2$—, —CH=CH—, —C≡C—, —(CH$_2$)$_4$— and —(CH$_2$)$_3$O—; and $R^1$ is selected from the group consisting of —CN, —COR, —COOR, —OCOR, —CONR'R, —NR'COR, OCOOR, —OCONR'R, —NR'COOR, —F, —Cl, —CF$_3$, —OCF$_3$, —OR and —R in which R is selected from the group consisting of hydrogen, an achiral C$_{1-18}$ alkyl group and an achiral C$_{4-18}$ is alkenyl group with the double bond at 3-position or higher; and R' is as defined above;

with the proviso that at most one of the rings A, B and C is a naphthalenediyl group.

In addition to the laterally substituted mesogenic compounds referred to above, such compounds are also disclosed in WO 95/24454 and WO 95/24455. However, many of these compounds are not suitable for preparing LCP films with high optical anisotropy without one or more of the aforementioned disadvantages. It has been found that by using the compounds of the present invention it is possible to control the optical anisotropy of LCPs without significant increase of melting point or decrease of clearing point. In addition they generally have a surprisingly low tendency to crystallise even far below the melting point (good supercoolability). Furthermore they generally exhibit enhanced alignment properties especially on structured LPP orientation layers, they are able to form tilt angles and show a decreased tendency to form tilt domains and disclinations. Furthermore the compounds of the invention have a comparatively good solubility in organic solvents and a high miscibility with other LCP compounds.

The optical anisotropy of the compounds of the invention may be easily adapted to requirements only by selecting different groups of M of formula I without changing the main core of the molecule. This allows an economical access to a broad range of LCPs exhibiting different optical anisotropies with a minimum of chemical steps in their production.

The polymerisable mesogenic residues $G^1$ and $G^2$ may be the same or different, but are preferably the same.

The group X is preferably selected from the group consisting of —CH$_2$—, —O—, —COO— and —OOC—.

The spacer group Sp may be optionally substituted by one or more fluorine or chlorine atoms. Groups in which there are no substituent groups present are preferred. It is especially preferred that the integer p has a value of from 1to 12 and that no more than two —CH$_2$— groups are replaced by —O— and that no more than one —CH$_2$— group is replaced by one group selected from the group consisting of —CH=CH—, —CO—, —COO—, —OOC—, —CONR'—, —OCOO— and —OCONR'.

The groups A and B comprising the achiral group M are either saturated, unsaturated or aromatic. They are optionally substituted by one or two substituents selected from the group consisting of F, Cl, CN, a lower alkyl, lower alkenyl, lower alkoxy and lower alkenyloxy. Preferably the groups A and B each contain no more that one substituent. It is especially preferred that the groups A and B contain no substitution.

It is preferred that the groups A and B are selected from the group consisting of 1,4-phenylene, pyridine-2,5-diyl, pyrimidine-2,5-diyl, trans-1,4-cyclohexylene or trans-1,3-dioxane-2,5-diyl, 1,4-naphthalenediyl and 2,6-naphthalenediyl. Is it especially preferred that A and B are selected from the group consisting of 1,4-phenylene, trans-1,4-cyclohexylene and 2,6-naphthalenediyl.

The group C comprising the achiral group M is either saturated, unsaturated or aromatic. It is optionally substituted with one or two substituents selected from the group consisting of F, Cl, CN, a lower alkyl, lower alkenyl, lower alkoxy and lower alkenyloxy. It is preferred that the group C contains at most one substituent. It is especially preferred that the group C contains no substitution.

It is preferred that the group C is selected from furan-2,4-diyl, furan-2,5-diyl, tetrahydrofuran-2,4-diyl, tetrahydrofuran-2,5-diyl, dioxolane-2,4-diyl, dioxolane-2,5-diyl, oxazole-2,4-diyl, oxazole-2,5-diyl, cyclopentane-1,3-diyl, cyclopentane-1,4-diyl, 1,4-phenylene, pyridine-2,5-diyl, pyrimidine-2,5-diyl, trans-1,4-cyclohexylene or dioxane-2,5-diyl, 1,4-naphthalenediyl and 2,6-naphthalenediyl. It is especially preferred that C is selected from the group consisting of furan-2,5-diyl, tetrahydrofuran-2,5-diyl, oxazole-2,5-diyl, 1,4-phenylene, trans-1,4-cyclohexylene, and 2,6-naphthalenediyl.

The group $Z^1$ comprising the achiral group M is preferably selected from the group consisting of —O—, —COO—, —OOC— and a single bond. It is especially preferred that $Z^1$ is selected from —O— or a single bond.

The groups $Z^2$ and $Z^3$ comprising the achiral group M are preferably selected from the group consisting of —COO—, —OOC—, —CH$_2$CH$_2$—, —CH$_2$O—, —OCH$_2$—, —CH=CH—, —C≡C— and a single bond. It is especially preferred that $Z^2$ and $Z^3$ are selected from the group consisting of —COO—, —OOC—, —C≡C— and a single bond.

The group $R^1$ comprising the achiral group M is preferably selected from the group consisting of —CN, —COOR, —OCOR, F, Cl, CF$_3$, OCF$_3$, OR, R, in which R represents a C$_{1-12}$ achiral alkyl, C$_{4-12}$ achiral alkenyl group with the double bond at position 3- or higher, or hydrogen. It is especially preferred that $R^1$ is selected from the group consisting of —CN, F, Cl, CF$_3$, OCF$_3$, OR, R, in which R represents a C$_{1-8}$ achiral alkyl group or hydrogen.

By the term "lower alkyl" it should be understood to include a C$_{1-6}$ achiral, branched or straight-chained alkyl group. Examples of lower alkyl groups that may be present in the compounds of the invention include methyl, ethyl, propyl, butyl, pentyl hexyl and the like.

By the term "lower alkenyl" it should be understood to include C$_{3-6}$ achiral, branched or straight-chained alkenyl group in which the double bond is at position 2- or higher. Examples of lower alkenyl groups that may be present in the compounds of the invention include 2-propenyl, 3-butenyl, 3-isopentenyl, 4-pentenyl, 5-hexenyl, 4-isohexenyl and the like.

By the term "lower alkoxy" it should be understood to include C$_{1-6}$; achiral, branched or straight-chained alkoxy group. Examples of lower alkoxy groups that may be present in the compounds of the invention include methoxy, ethoxy, propoxy, butoxy, pentoxy hexoxy and the like.

By the term "alkenyloxy" it should be understood to include C$_{3-6}$ achiral, branched or straight-chained alkenyloxy group in which the double bond is at position 2- or higher. Examples of lower alkenyloxy groups that may be present in the compounds of the invention include 2-propenyloxy, 3-butenyloxy, 4-pentenyloxy, 5-hexenyloxy and the like.

Preferably the polymerisable mesogenic residues $G^1$ and $G^2$ are each independently represented by the group of formula III

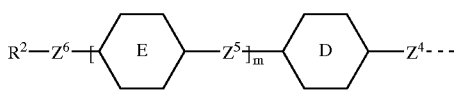

wherein
- D and E are independently selected from the group consisting of 1,4-phenylene, pyridine-2,5-diyl, pyrimidine-2,5-diyl, trans-1,4-cyclohexylene and trans-1,3-dioxane-2,5-diyl;
- m is 1 or 0,
- $Z^4$ and $Z^5$ are independently selected from the group consisting of a single bond, —COO—, —OOC—, —CH$_2$—CH$_2$—, —CH$_2$O—, —OCH$_2$—, —CH=CH—, —C≡C—, —(CH$_2$)$_4$— and —(CH$_2$)$_3$O—;
- $Z^6$ represent a group of formula —(CH$_2$)$_p$X— in which p is an integer having a value of 1 to 18 and X is defined above, and in which one or two non adjacent —CH$_2$— groups may be optionally replaced by —CH=CH— or in which one or two —CH$_2$— groups may be replaced by one or two additional linking groups X with the proviso that firstly the group $Z^6$ does not contain two adjacent heteroatoms and secondly when X is —CH$_2$, p can also have a value of 0
- $R^2$ represents a polymerisable group selected from the group consisting of CH$_2$=C(Ph)—, CH$_2$=CW—COO—, CH$_2$=CH—COO—Ph—, CH$_2$=CW—CO—NH—, CH$_2$=CH—O—, CH$_2$=CH—OOC—, Ph—CH=CH—, CH$_2$=CH—Ph—, CH$_2$=CH—Ph—O—, $R^3$—Ph—CH=CH—COO—, $R^3$—OOC—CH=CH—Ph—O— and 2-W-epoxyethyl in which
- W represents H, Cl, Ph or a lower alkyl,
- $R^3$ represents a lower alkyl with the proviso that when $R^3$ is attached to a phenylene group (—Ph—) it may also represent hydrogen or a lower alkoxy.

The terms "Ph" and "Ph—" will be understood to indicate a phenyl group. The term "—Ph—" will be understood to mean any isomer of phenylene, namely 1,2-phenylene, 1,3-phenlylene or 1,4-phenylene, except where the context requires otherwise.

The groups D and E are optionally substituted with one or two halogens, —CN, lower alkyl, lower alkenyl, lower alkoxy or lower alkenyloxy groups. If halogen substituents are present they are preferably F or Cl. It is preferred that the groups D and E are selected from optionally substituted 1,4-phenylene and 1,4-cyclohexylene rings. It is especially preferred that the groups D and E contain no substitution.

It is preferred that the groups $Z^4$ and $Z^5$ are selected from the group consisting of a single bond, —COO—, —OOC—, —CH$_2$—CH$_2$—, —CH$_2$O—, —OCH$_2$—, —CH=CH— and —C≡C—. It is especially preferred that $Z^4$ and $Z^5$ represent a single bond, —C≡C—, —COO— or —OOC—.

$Z^6$ may be optionally substituted by one or more halogen atoms, preferably one or more fluorine atoms. It is preferred that p has a value of 1 to 11. It is also preferred that $Z^6$ contains no substitution. It is further preferred that, for the group $Z^6$, X is selected from —CH$_2$—, —O—, —COO— and —OOC—, especially —CH$_2$— or —O—.

It is preferred that the group $R^2$ is selected from the group consisting of CH$_2$=CW—COO— and CH$_2$=CH—O—.

It is preferred that the sum of the two integers m for each of the groups $G^1$ and $G^2$ is 0 or 1. It is especially preferred that for both $G^1$ and $G^2$ m has a value of 0.

The compounds of the invention may be readily prepared using procedures well known to a skilled person in accordance with any one of the procedures set out in Schemes 1 and 2 below.

Scheme 1

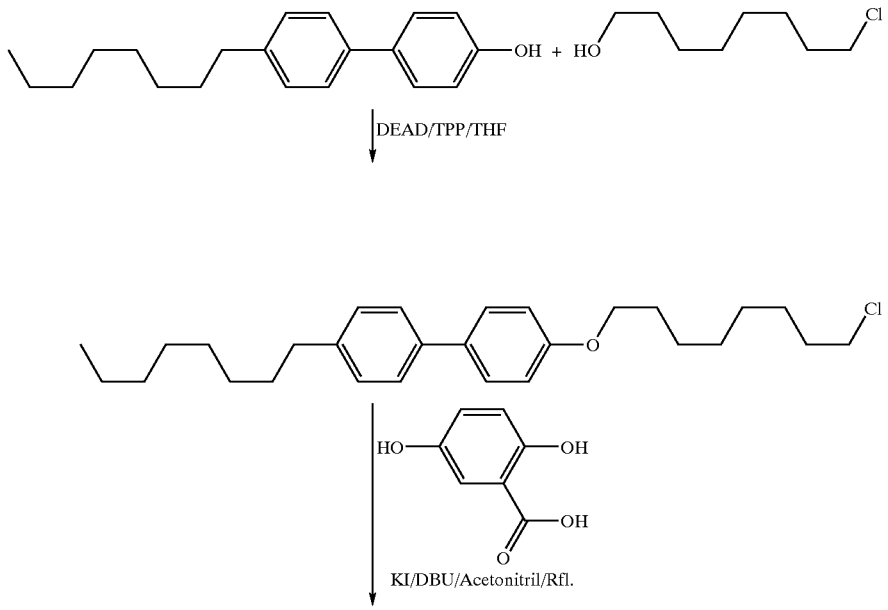

-continued
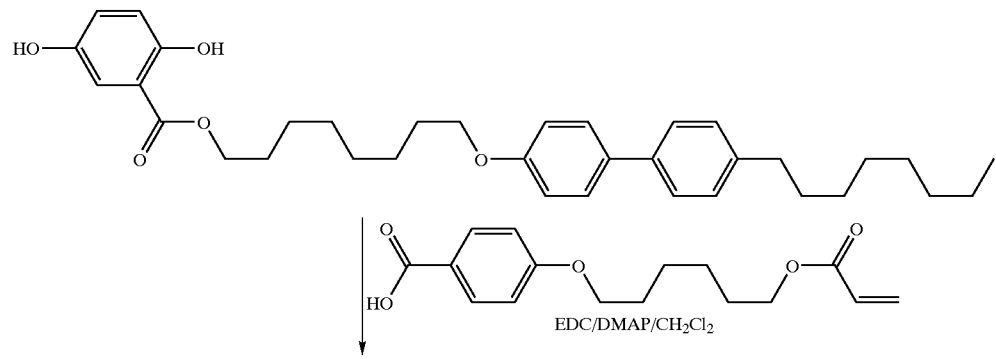
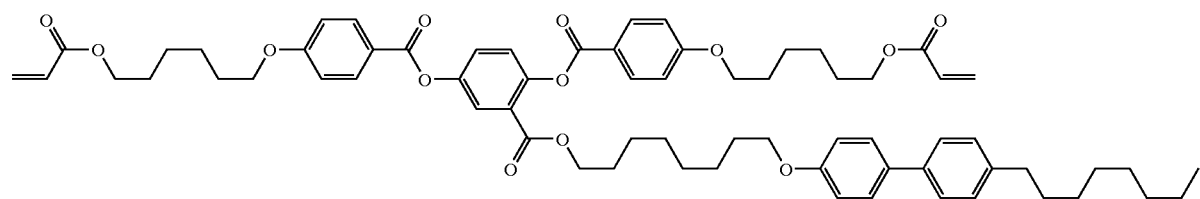
Scheme 2
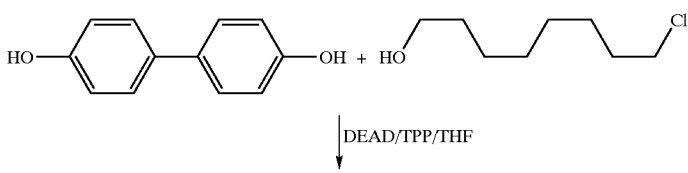
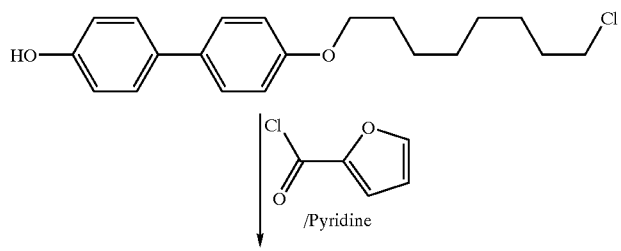
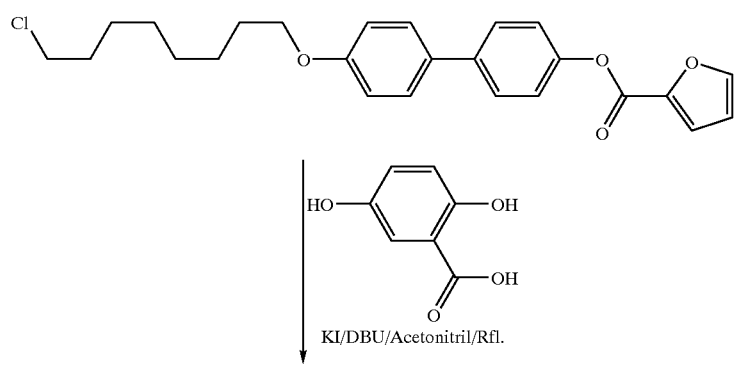

-continued

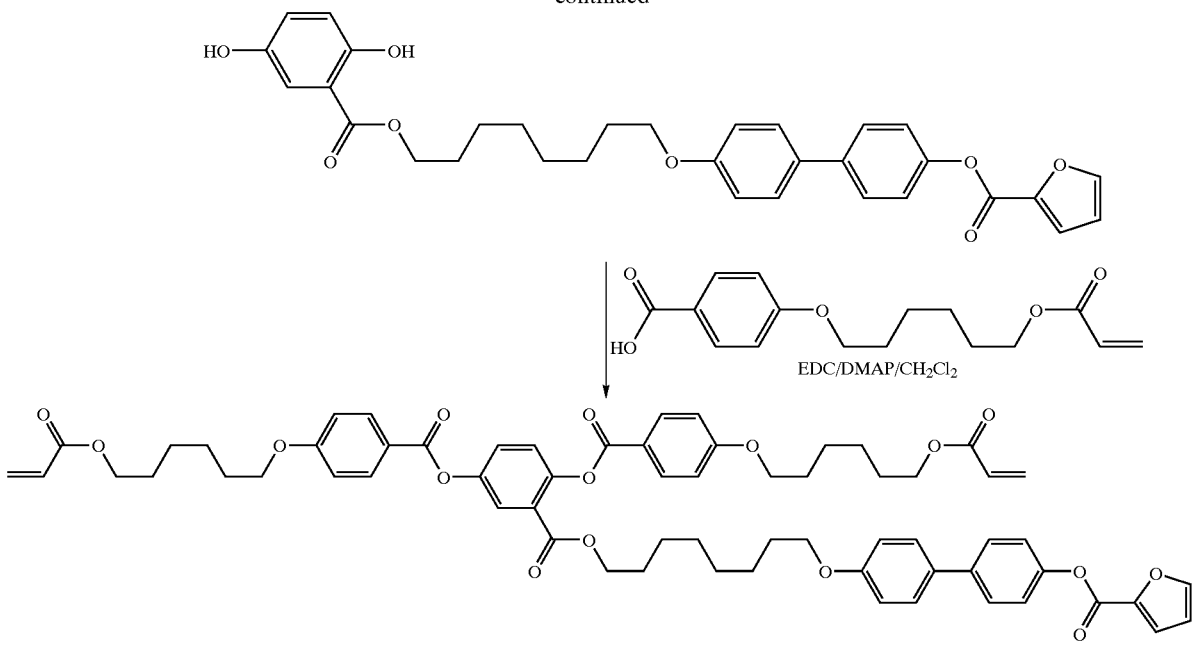

in which:
DEAD is diethyl azodicarboxylate
TPP is triphenylphospine
THF is tetrahydrofuran
KI is potassium iodide
DBU is 1,8-diazabicyclo[5.4.0]undec-7-ene
EDC is N-(3-dimethylaminopropyl)-N'-ethylcarbodiimide hydrochloride
DMAP is 4-dimethylaminopyridine Suitable starting materials used in the preparation of the compounds of the present invention include, amongst others, phenyl and biphenyl alcohol and carboxylic acid compounds as well as 1,4-cyclohexanedione. The starting materials are commercially available or may be readily prepared and are well known to a skilled person.

The compounds of the invention are preferably prepared by forming a ring that includes a lateral group prior to linking the mesogenic residues. Alternatively, the compounds may be prepared by forming a ring that includes a polymerisable mesogenic residue prior to linking the lateral group. A second aspect of the invention therefore provides a method of preparation of a compound of formula (I), the method comprising forming a ring that includes a lateral group and subsequently linking the mesogenic residue thereto. The mesogenic residues $G^1$ and $G^2$ are preferably connected to the central ring simultaneously. As indicated above, it is especially preferred that the mesogenic residues $G^1$ and $G^2$ are identical.

It will be appreciated that the compounds of the invention may be used in the preparation of liquid crystalline mixtures. Such mixtures may be prepared by admixing a compound of formula (I) with one or more additional components. An organic solvent may also be used in the preparation of these mixtures. A third aspect of the invention therefore provides a liquid crystalline mixture comprising a compound of formula (I) and one or more additional components. The one or more additional components present in the liquid crystalline mixture may be further compounds of formula (I), other mesogenic compounds, compounds that are compatible with a mesogenic molecular architecture or chiral dopants for the induction of helical pitch. The LCP mixture may also include a suitable organic solvent. Examples of solvents that may be used in the preparation of such liquid crystalline mixtures include anisole, N-methylmorpholine, caprolactone, cyclohexanone, methyl ethyl ketone and the like.

Examples of additional components that may be used in the preparation of liquid crystalline LCP mixtures according to the third aspect of the invention include those compounds represented by formulae III to X.

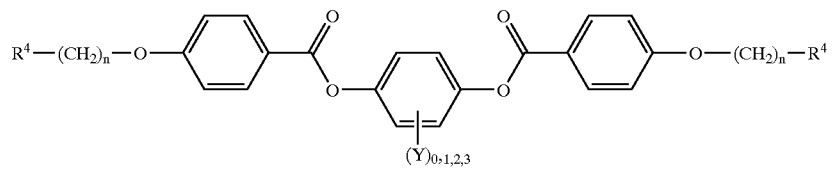

III

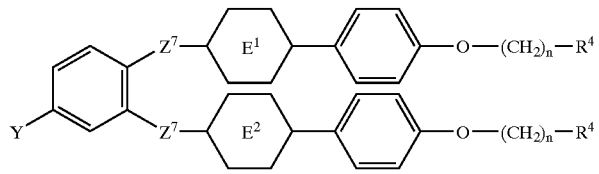
IV
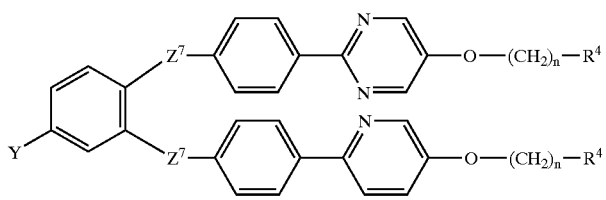
V
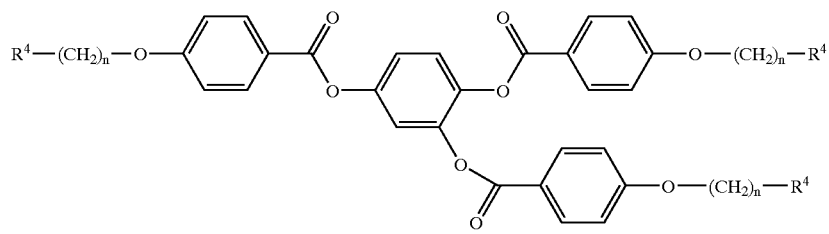
VI
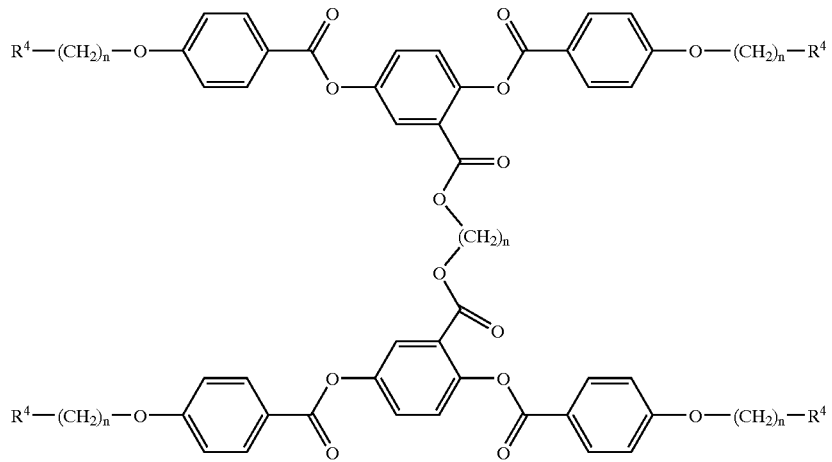
VII

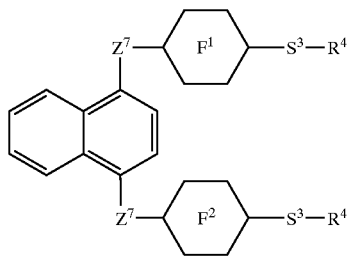

VIII

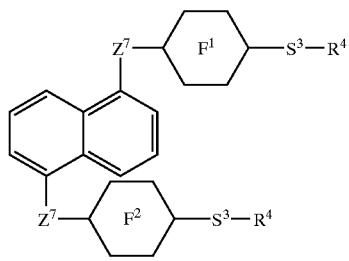

IX

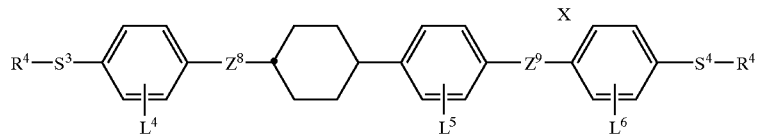

X in which

R⁴ is selected from the group consisting of CH₂=CH—O—, CH₂=CH—COO—, CH₂=C(CH₃)—COO—, CH₂=C(Cl)—COO— and

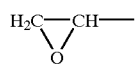

$S^3$, $S^4$ independently represent —(CH₂)$_n$— or —O(CH₂)$_n$—;

$E^1$, $E^2$ are independently selected from the group consisting of 1,4-phenylene trans-1,4-cyclohexylene, pyridine-2,5-diyl, pyrimidine-2,5-diyl and trans 1,4-cyclohexylene-1,4-phenylene;

$F^1$, $F^2$ are independently selected from the group consisting of 1,4-phenylene, and 2- or 3-fluoro-1,4-phenylene;

$L^4$, $L^5$, $L^6$ are independently selected from the group consisting of OH, $C_1$–$C_{20}$-alkyl, $C_1$–$C_{20}$-alkenyl, $C_1$–$C_{20}$-alkoxy, $C_1$–$C_{20}$-alkoxy-carbonyl, formyl, $C_1$–$C_{20}$-alkylcarbonyl, $C_1$–$C_{20}$-alkylcarbonyloxy, halogen, cyano and nitro;

$Z^7$ is selected from the group consisting of —COO—, —OOC—, —OCH₂—, —CH₂O—, —O(CH₂)₃—, —OOC(CH₂)₂— and —COO(CH₂)₃—;

$Z^8$ is selected from the group consisting of a single bond, —CH₂CH₂—, —CH₂O—, —OCH₂—, —COO—, —OOC—, —(CH₂)₄—, —O(CH₂)₃—, (CH₂)₃O— and —C≡C—;

$Z^9$ is selected from the group consisting of a single bond, —CH₂CH₂—, —CH₂O—, —OCH₂—, —COO—, —OOC—, and —C≡C—;

Y is independently selected from the group consisting of hydroxy, $C_1$–$C_{20}$-alkyl, $C_1$–$C_{20}$-alkenyl, $C_1$–$C_{20}$-alkoxy, $C_1$–$C_{20}$-alkoxycarbonyl, formyl-, $C_1$–$C_{20}$-alkylcarbonyl, $C_1$–$C_{20}$-alkylcarbonyloxy, fluoro, chloro, bromo, cyano and nitro;

n is an integer having a value of from 2 to 20; and v is an integer having a value of from 2 to 12

The compounds of the invention may also be used in the formation of a LCP layer by casting a LCP compound according to the first aspect of the invention or a mixture according to the third aspect of the invention onto a substrate. A fourth aspect of the invention therefore provides a method forming a LCP network comprising forming a LCP layer including a compound of formula (I) and cross-linking the layer. Liquid crystalline mixtures according to the third aspect of the invention may also be used in the manufacture of LCP networks in a similar way.

The invention also includes, in a fifth aspect of the invention, a cross-linked LCP network comprising a compound of formula (I) in a cross-linked form. Cross-linked LCP networks comprising a mixture according to the third aspect of the invention in cross-linked form may also be included in this aspect of the invention.

A sixth aspect of the invention provides the use of a compound of formula (I) in the preparation of an optical or an electro-optical device. The use, in the preparation of an optical or electro-optical device, of liquid crystalline mixtures according to the third aspect of the invention is also included in this aspect of the invention.

A seventh aspect of the invention provides an optical or an electro-optical device comprising a compound of formula (I) in a cross-linked state. An optical or electro-optical device comprising a LCP liquid crystalline mixture in a cross-linked state according to the third aspect of the invention is also included in this aspect of the invention.

The invention will now be described with reference to the following non-limiting examples. These examples are provided by way of illustration only. Variations on these examples falling within the scope of the invention will be apparent to a skilled person.

EXAMPLES

Example 1

Synthesis of 8-Chlorooctyl-4-(4'-octylbiphenyl) ether

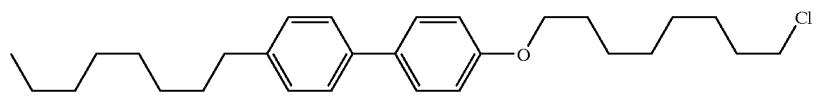

A solution of diethyl azodicarboxylate (2.1 g; 12 mmol) tetrahydrofuran (10 ml) was added dropwise at 0° C. to a solution of 4-octyl-4'-hydroxybiphenyl (3.2 g; 11.3 mmol), 8-chlorooctanol (1.9 g; 12 mmol), triphenylphosphine (3.2 g; 12 mmol) and tetrahydrofuran (80 ml) and stirred at room temperature overnight. The reaction mixture was added to water (200 ml) and extracted with ethyl acetate (3×100 ml). The combined organic layers were washed with water (2×100 ml), dried over magnesium sulphate and filtered. The solvent was removed in vacuo. The residue (11.1 g) was purified by flash chromatography on silica gel column using a toluene/ethyl acetate mixture (95:5) as eluent to give 4.4 g (93%) of 8-Chlorooctyl-4-(4'-octylbiphenyl) ether.

Synthesis of 8[(4'-Octyl-4-biphenylyl)oxy]octyl 2,5-dihydroxybenzoate

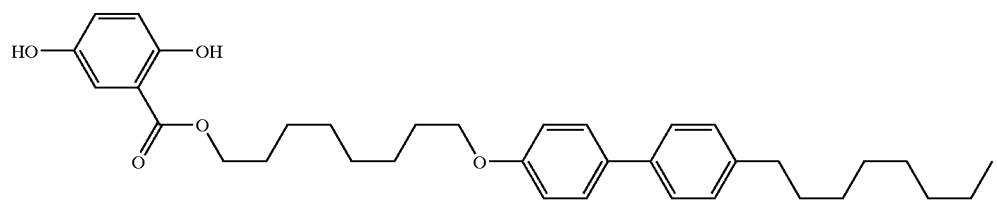

A mixture of 2,5-dihydroxybenzoic acid (1.7 g; 11.0 mmol), 1,8-diazabicyclo-[5.4.0]undec-7-ene (1.7 g; 11.0 mmol), 8-chlorooctyl-4'-octyl-4-biphenyl ether (4.4 g; 10.2 mmol), potassium iodide (6.6 g; 40.0 mmol) and acetonitrile (150 ml) was heated under reflux for 72 h. The reaction mixture was cooled, poured into water (600 ml) and extracted with ethyl acetate (3×150 ml). The combined organic layers were washed with 1N-hydrochloric acid (150 ml) and water (2×150 ml), dried over magnesium sulphate and filtered. The solvent was removed in vacuo. The residue (4.9 g) was purified by recrystallisation from ethyl acetate/toluene to give 4.5 g (80%) of 8-[(4'-octyl-4-biphenylyl)oxy]octyl 2,5-dihydroxybenzoate.

Synthesis of [[[8-[(4'-Octyl-4-biphenyl)oxy]octyl]oxy]carbonyl]-p-phenylene bis[p-[[6-(acryloyloxy)hexyl]oxy]benzoate]

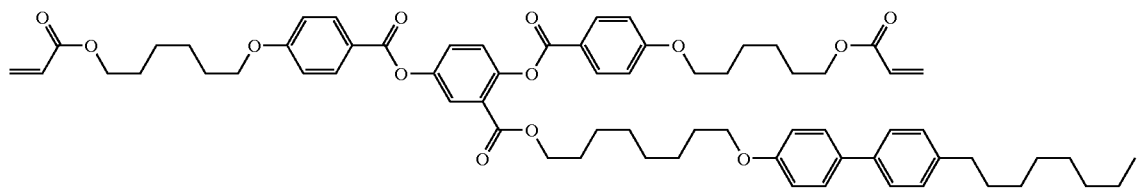

A solution of N-(3-dimethylaminopropyl)-N'-ethyl-carbodiimide hydrochloride (2.6 g; 13.7 mmol) in dichloromethane (50 ml) was added slowly to a solution of 8-[(4'-octyl-4-biphenylyl)oxy]octyl-2,5-dihydroxybenzoate (3.0 g; 5.5 mmol), 4-(6-acryloyl-hexyloxy)benzoic acid (4.1 g; 13.7 mmol) and 4-dimethylaminopyridine (1.3 g; 10.9 mmol) in dichloromethane (100 ml) at 0° C. The mixture was stirred at room temperature overnight, added to water (200 ml) and extracted with dichloromethane (3×100 ml). The combined organic layers were washed with water (2×100 ml), dried over magnesium sulphate and filtered. The solvent was removed in vacuo. The residue (8.4 g) was purified by flash chromatography on silica gel column using a toluene/ethyl acetate mixture (95:5) as eluent. Recrystallisation from ethyl acetate/hexane gave 2.2 g (38%) of [[[8-[(4'-octyl-4-biphenyl)oxy]octyl]oxy]carbonyl]-p-phenylene bis[p-[[6-(acryloyl-oxy)hexyl]oxy]benzoate]. Mp (C—N)=89.5° C.; Clp (N—I)=103° C.

The following compounds were synthesised using a similar method.

2,5-bis-[4-(6-Acryloyloxyhexyloxy)benzoyloxy]benzoic Acid 8-[4-(5-Octylpyridin-2-yl)phenoxy]nonyl Ester

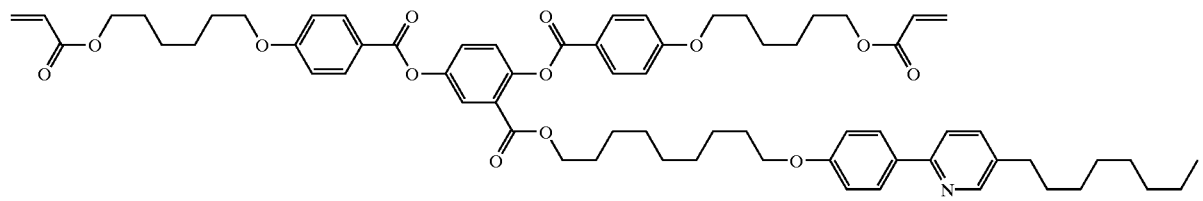

Mp (C—N)=61° C.; Clp (N—I)=89° C.

[[[9-[p-(5-Nonyl-2-pyrimidinyl)phenoxy]nonyl]oxy]carbonyl]-p-phenylene bis[p-[[6-(acryloyloxy)hexyl]oxy]benzoate]

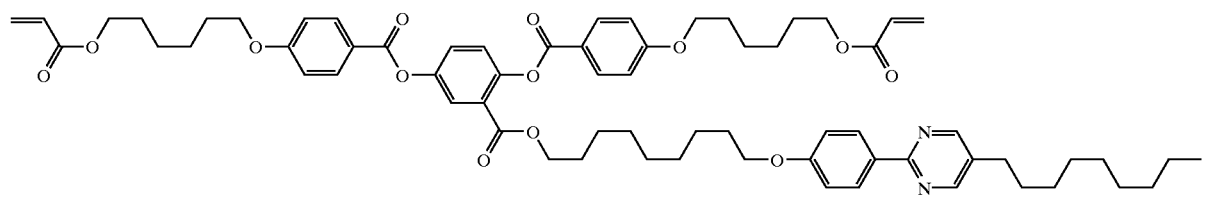

Mp (C—N)=55.5° C.; Clp (N—I)=90.2° C.

[[[8-[p-(Trans-4-pentylcyclohexyl)phenoxy]octyl]oxy]carbonyl]-p-phenylene bis[p-[[6-(acryloyloxy)hexyl]oxy]benzoate]

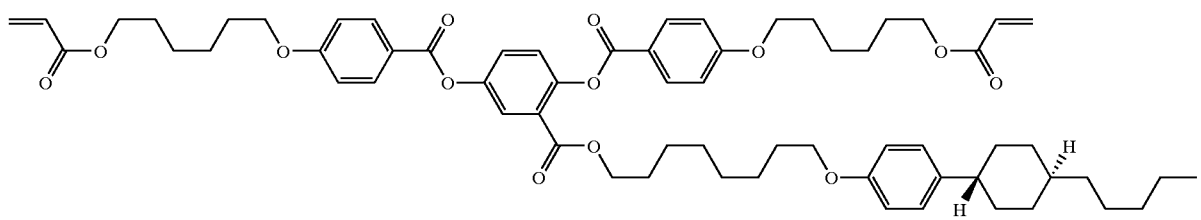
[[[[8-[(4'-Cyano-4-biphenylyl)oxy]octyl]oxy]carbonyl]-p-phenylene bis[p-[[6-(acryloyloxy)hexyl]oxy]benzoate]
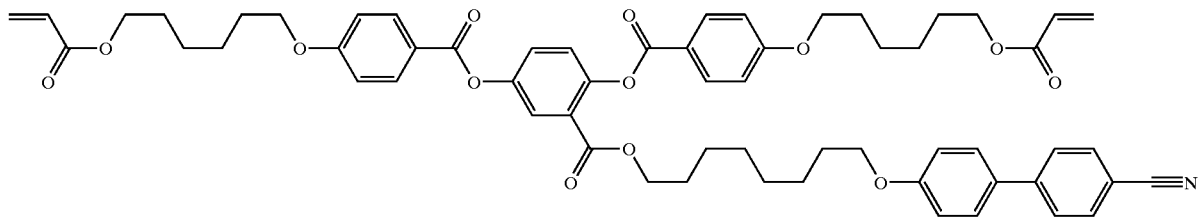
Mp (C—N)=72° C.; Clp (N—I)=114.7° C. Solubility in MPK: 7.2%
2,5-Bis[4-(6-acryloyloxyhexyloxy)benzoyloxy]benzoic Acid 8-(6-Pentyloxy-2-naphthyloxy)octyl Ester
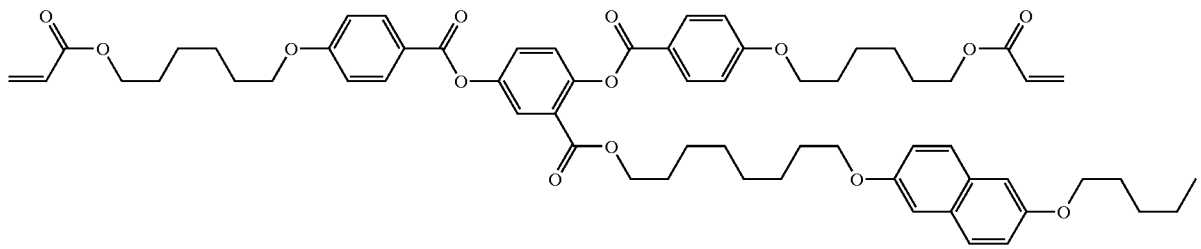
[[2-[2-[(4'Cyano-4-biphenyl)oxy]ethoxy]ethoxy]carbonyl]-p-phenylene bis[p-[6-(Acryloyloxy)hexyloxy]benzoate
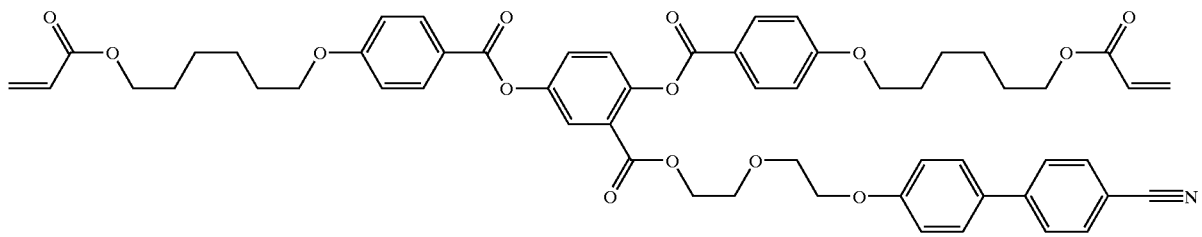

Mp. (C—N)=54° C.; Clp (N—I)=86° C.; Solubility, in MPK: 33.2%

2,5-Bis[4-(6-acryloyloxyhexyloxy)benzoyloxy]benzoic Acid 6-[4-[(4-Cyanophenyl) ethinyl]phenyloxy]hexyl Ester

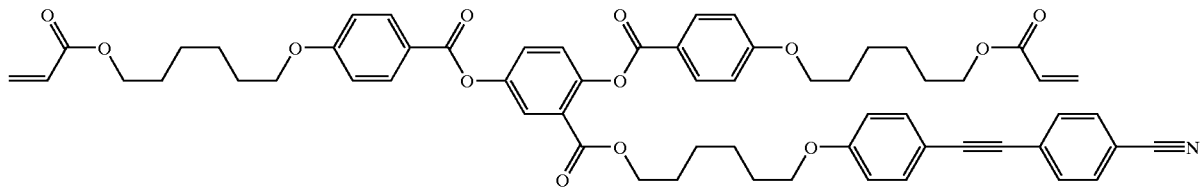

Mp. (C—N)=71.4° C.; Clp (N—I)=130.6C;
2,5-Bis[4-(6-acryloyloxy)hexyloxy)benzoyloxy]benzoic Acid 8-(2-Naphthyloxy)octyl Ester

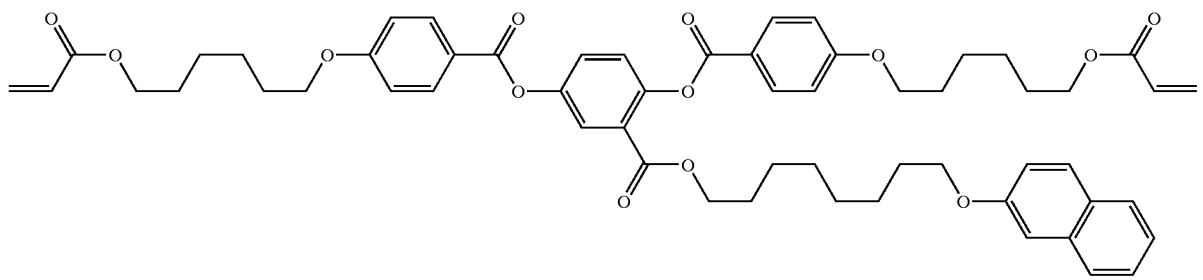

Mp. (C—N)=63° C.; Clp (N—I)=74° C.; This compound may be supercooled

Example 2

Synthesis of 4'-[(8-Chlorooctyl)oxy]-4-biphenylol

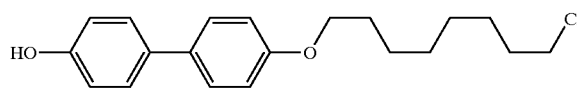

A solution of diethyl azodicarboxylate (3.5 g; 20 mmol) and tetrahydrofuran (10 ml) was added dropwise at 0° C. to a solution of 4,4'-dihydroxybiphenyl (7.4 g; 40 mmol), 8-chloro-1-octanol (3.3 g; 20 mmol), triphenylphosphine (5.2 g; 20 mmol) and tetrahydrofuran (120 ml) and stirred at room temperature 72 h. The reaction mixture was added to water (400 ml) and extracted with ethyl acetate (3×150 ml). The combined organic layers were washed with water (2×150 ml), dried over magnesium sulphate and filtered. The solvent was removed in vacuo. The residue (19.2 g) was purified by flash chromatography on a silica gel column using a toluene/ethyl acetate mixture (95:5) as eluent, to give 2.6 g (40%) of 4'-[(8-chlorooctyl)oxy]-4-biphenylol.

Synthesis of 4'-[(8-Chlorooctyl)oxy]-4-biphenylyl 2-furoate

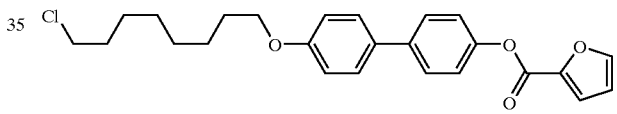

A solution of 2-furoyl chloride (1.3 g; 9.8 mmol) was added dropwise at 0° C. to a solution of 4'-[(8-chlorooctyl) oxy]-4-biphenylol (2.6 g; 7.8 mmol) and pyridine (20 g; 253 mmol), stirred at room temperature overnight. The resulting mixture was added to 1N-hydrochloric acid (200 ml) and extracted with ethyl acetate (3×100 ml). The combined organic layers were washed with saturated sodium chloride solution (2×80 ml), dried over magnesium sulphate and filtered. The solvent was removed in vacuo. The residue (3.3 g) was purified by recrystallisation from ethyl acetate/ hexane, to give 2.9 g (88%) of 4-[(8-Chlorooctyl)oxy]-4-biphenylyl-2-furoate.

Synthesis of {[8-[(2,5-Dihydroxybenzoyl)oxy]octyl] oxy}-4-biphenylyl 2-furoate

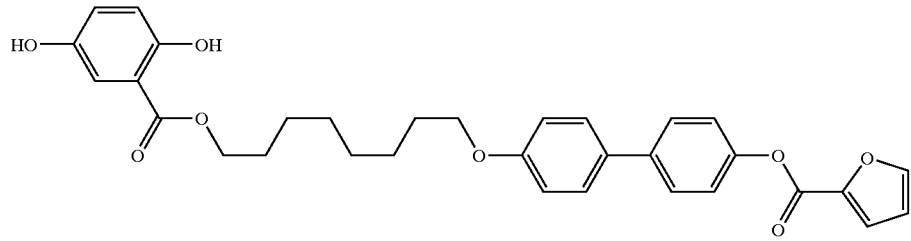

A mixture of 2,5-dihydroxybenzoic acid (1.1 g; 7.0 mmol), 1.8-diazabicyclo-[5.4.0]undec-7-ene (1.1 g; 7.0 mmol), 4'-[(8-chlorooctyl)oxy]-4biphenyl-2-furoate (2.9 g; 6.8 mmol), potassium iodide (5.2 g; 35 mmol) and acetonitrile (100 ml) was heated under reflux for 48 h. The cooled reaction mixture was poured into water (500 ml) and extracted with ethyl acetate (3×150 ml). The combined organic layers were washed with 1N-hydrochloric acid (100 ml) and water (2×100 ml), dried over magnesium sulphate and filtered. The solvent was removed in vacuo. The residue (2.8 g) was purified by flash chromatography on a silica gel column using a toluene/ethyl acetate mixture (93:7) as eluent to give 1.1 g (30%) of {[8-[(2,5-dihydroxybenzoyl) oxy]octyl]oxy}-4-biphenylyl-2-furoate.

Synthesis of Furan-2-carboxylic Acid 4'-(8-{2,5-bis-[4-(6-Acryloyloxyhexyloxy)-benzoyloxy] benzoyloxy}octyloxy)biphenyl-4-yl Ester

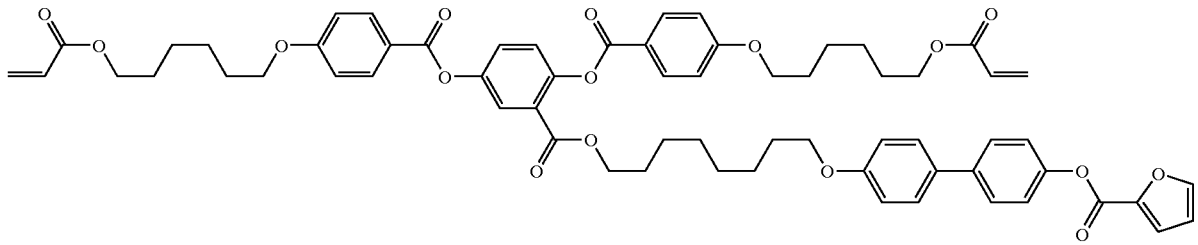

A solution of N-(3-dimethylaminopropyl)-N'-ethyl-carbodiimide hydrochloride (1.0 g; 5.1 mmol) in dichloromethane (20 ml) was slowly added to a solution of 4'-{[8-[(2,5-dihydroxybenzoyl)oxy]octyl]oxy}-4-biphenylyl-2-furoate (1.1 g; 2.0 mmol), 4-(6-acryloylhexyloxy)benzoic acid (1.5 g; 5.0 mmol) and 4-dimethylaminopyridine (0.5 g; 3.9 mmol) in dichloromethane (30 ml) at 0° C. The mixture was stirred overnight at room temperature, added to water (200 ml) and extracted with dichloromethane (3×100 ml). The organic layers were washed with water (2×80 ml), dried over magnesium sulphate and filtered. The solvent was removed in vacuo. The residue (2.6 g) was purified by flash chromatography on a silica gel column using a toluene/ethyl acetate mixture (90:10) as eluent. Recrystallisation from ethyl acetate/isopropanol gave 0.4 g (19%) of furan-2-carboxylic acid 4'-8-{2,5-bis[4-(6-acryloyloxyhexyloxy)benzoyloxy]-benzoyloxy}octyloxy)biphenyl-4-yl ester.

Mp (C—N)=89.5° C.; Clp=103° C. The compound is supercoolable below room temperature.

2,5-Bis[4-(6-acryloyloxyhexyloxy)benzoyloxy]benzoic Acid 8-[6-[(4-Octyloxyphenyl)ethinyl]-2-naphthyloxy] hexyl Ester

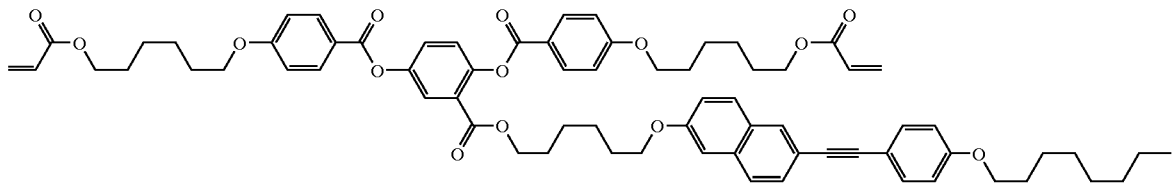

60

Mp. (C—N)=67° C.; Clp (N—I)=145° C.; This compound may be supercooled 2,5-Bis[4-(6-acryloyloxyhexyloxy)benzoyloxy]benzoic Acid 8-[6-[(4-Cyanophenyl) ethinyl]-2-naphthyloxy]octyl Ester

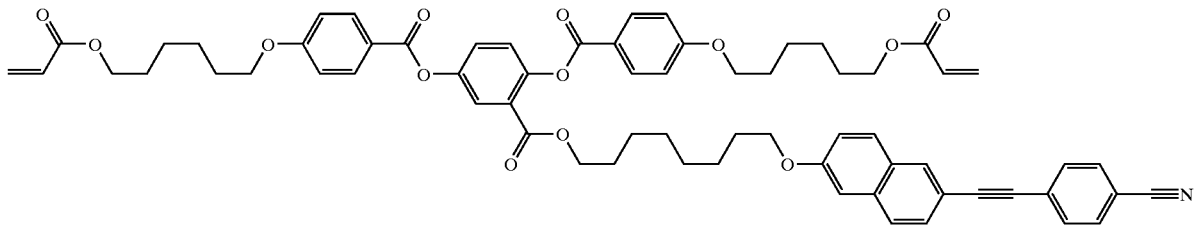

Mp. (C—N)=103° C.; Clp (N—I)=142° C.; This compound may be supercooled

[[2-[2-[2-[(4-Cyanophenyl)ethinyl]-6-naphthyloxy]ethoxy]ethoxy]carbonyl]-p-phenylene bis[p-[6-(acryloyloxy)hexyloxy]benzoate

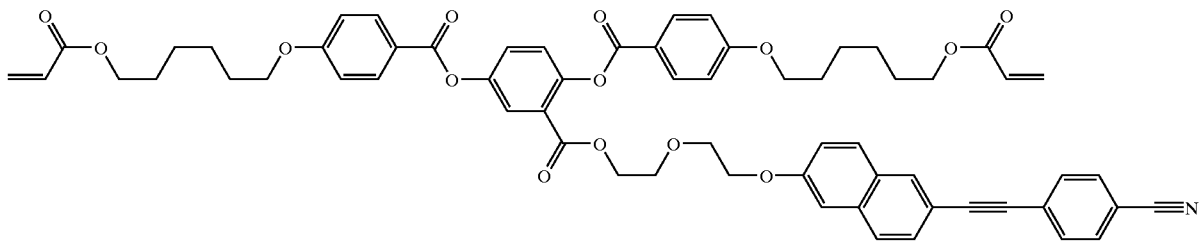

Mp. (C—N)=90° C.; Clp (N—I)=133° C.; This compound may be supercooled

[[2-[2-[4'-[(4-Cyanophenyl)ethinyl]-4-biphenyloxy]ethoxy]ethoxy]carbonyl]-p-phenylene bis[p-[6-(acryloyloxy)hexyloxy]benzoate

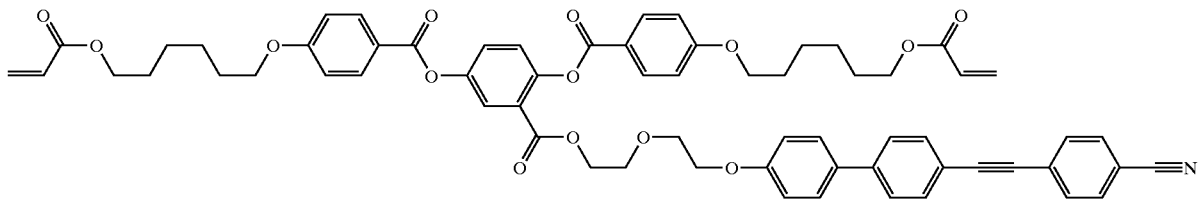

Mp. (C—N)=93° C.; Clp (N—I)=177° C.; This compound may be supercooled

Example 3

Preparation of Nematic LCP films (i) A mixture of the following components in anisole was prepared:

60 wt % of

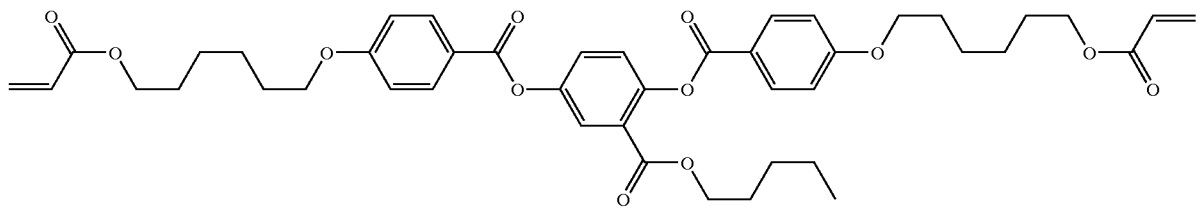

20 wt % of

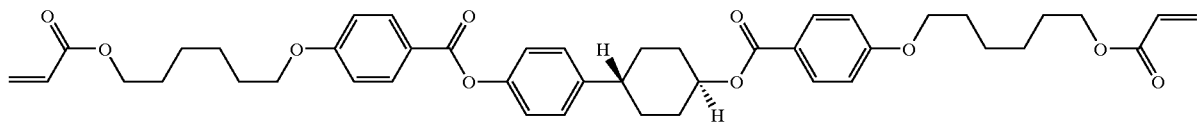

10 wt % of

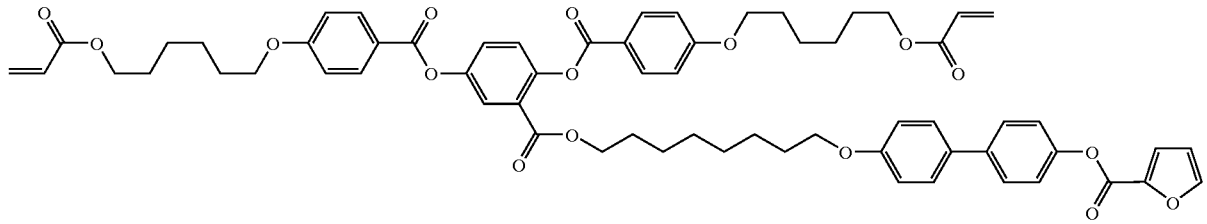

and 10 wt % of 1,4-butanediol diacrylate as a promoter of forming a polymer network. Further 500 ppm of 2,6-di-(t-butyl)-4-hydroxytoluene (BHT) inhibitor were added to this mixture in order to prevent untimely polymerisation. Polymerisation was started using 500 ppm initiator such as Irgacure 369 (commercially available from Ciba Geigy, Basle, Switzerland). The mixture was stirred at room temperature and than spincoated on a glass plate having an orientation layer to form an LCP film of ca. 800 nm in thickness. This film was dried at 50° C. for 1 or 2 minutes and photopolymerised by irradiation with UV light for approximately 5 minutes at room temperature in a $N_2$ atmosphere using a mercury lamp.

The well oriented film shows the nematic mesophase at room temperature.

(ii) A mixture of the following components in Anisole was prepared according to the procedure of Example 1

60 wt % of

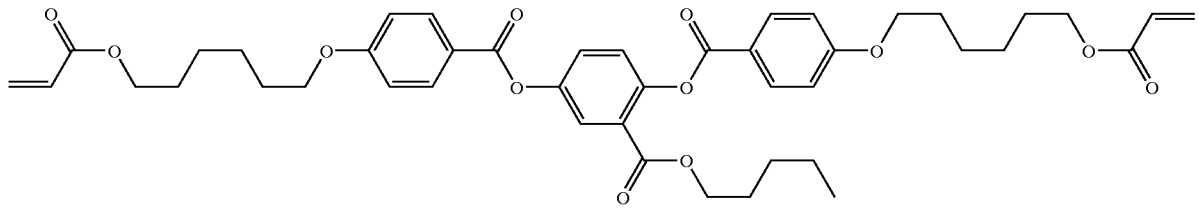

20 wt % of

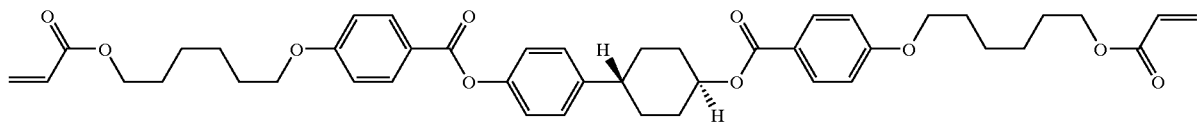

10 wt % of

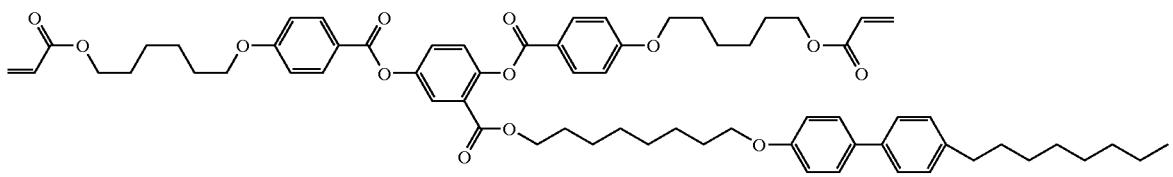

and 10 wt % of 1,4-butanediol diacrylate (Aldrich).

This nematic film also shows a well oriented nematic mesophase at room temperature with a clearing point of about 85° C. In addition this film exhibits a tilt angle of about 1° relative to the plane of the substrate, as shown by ellipsometric measurements.

What is claimed is:

1. A compound of formula (I)

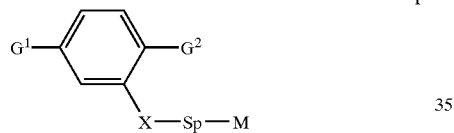

wherein
G$^1$ and G$^2$ independently represent a polymerisable mesogenic residue;
X represents a group selected from —CH$_2$—, —O—, —CO—, —COO—, —OOC—, —CONR'—, —OCOO—, —OCONR';
Sp represents a group of the formula —(CH$_2$)$_p$— in which p is an integer of 1 to 18 and in which one or two non adjacent —CH$_2$— groups are optionally replaced by —CH=CH—; or in which one or two —CH$_2$— groups are optionally replaced by one or two groups selected from the group consisting of —O—, —CO—, —COO—, —OOC—, —CONR'—, —OCOO—, and —OCONR' with the proviso that firstly the spacer group does not contain two adjacent heteroatoms and secondly when X is —CH$_2$—, p can also have a value of 0; and
M represents an achiral group of formula (II)

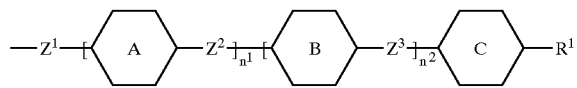

in which
A and B independently represent an optionally substituted six membered isocyclic or heterocyclic group or naphthalenediyl;
C is selected from the group consisting of an optionally substituted five and six membered isocyclic or heterocyclic group or naphthalenediyl;

$n^1$ and $n^2$ are 0 or 1 with the proviso that firstly $1 \leq n^1 + n^2 \leq 2$ and secondly, when C is naphthalenediyl $0 \leq n_1 + n^2 \leq 2$;
Z$^1$ is selected from the group consisting of —O—, —COO—, —OOC—, —CO—, —CONR'—, —NR'CO—, OCOO—, —OCONR'—, —NR'COO— and a single bond;
in which
R' is selected from the group consisting of hydrogen, a lower achiral alkyl group and a lower achiral alkenyl group;
Z$^2$ and Z$^3$ are independently selected from the group consisting of a single bond, —COO—, —OOC—, —CH$_2$—CH$_2$—, —CH$_2$O—, —OCH$_2$—, —CH=CH—, —C≡C—, —(CH$_2$)$_4$—, and —(CH$_2$)$_3$O—; and
R$^1$ is selected from the group consisting of —CN, —COR, —COOR, —OCOR, —CONR'R, —NR'COR, OCOOR, —OCONR'R, —NR'COOR, —F, —Cl, —CF$_3$, —OCF$_3$, —OR and —R
in which
R is selected from the group consisting of hydrogen, an achiral C$_{1-18}$ alkyl group and an achiral C$_{4-18}$ alkenyl group with the double bond at 3-position or higher; and
R' is a defined above;
with the proviso that at most one of the rings A, B and C is a naphthalenediyl group.

2. A compound according to claim 1, in which G$^1$ and G$^2$ are the same.

3. A compound according to claim 1, in which X is selected from —CH$_2$—, —O—, —COO— and —OOC—.

4. A compound according to claim 1, in which the integer p of the group Sp has a value of from 1 to 12.

5. A compound according to claim 1, in which one or two —CH$_2$— groups in Sp are replaced by —O—.

6. A compound according to claim 1, in which no more than one —CH$_2$— group in Sp is replaced by a group selected from the group consisting of —CH=CH—, —CO—, —COO—, —OOC—, —CONR'—, —OCOO— and —OCONR'.

7. A compound according to claim 1, in which the groups A and B are selected from the group consisting of 1,4-phenylene, pyridine-2,5-diyl, pyrimidine-2,5-diyl, trans-1,4-cyclohexylene or trans-1,3-dioxane-2,5-diyl, 1,4-naphthalenediyl and 2,6-naphthalenediyl.

8. A compound according to claim 1, in which the group C is selected from furan-2,4-diyl, furan-2,5-diyl, tetrahydrofuran-2,4-diyl, tetrahydrofuran-2,5-diyl, dioxolane-2,4-diyl, dioxolane-2,5-diyl, oxazole-2,4-diyl, oxazole-2,5-diyl, cyclopentane-1,3-diyl, cyclopentane-1,4-diyl, 1,4-phenylene, pyridine-2,5-diyl, pyrimidine-2,5-diyl, trans-1,4-cyclohexylene or dioxane-2,5-diyl, and 2,6-naphthalenediyl.

9. A compound according to claim 1, in which the group $Z^1$ is selected from the group consisting of —O—, —COO—, —OOC— and a single bond.

10. A compound according to claim 1, in which the groups $Z^2$ and $Z^3$ are independently selected from the group consisting of —COO—, —OOC—, —CH$_2$CH$_2$—, —CH$_2$O—, —OCH$_2$—, —CH=CH—, —C≡C— and a single bond.

11. A compound according to claim 1, in which the group $R^1$ is selected from the group consisting of —CN, —COOR, —OCOR, F, Cl, CF$_3$, OCF$_3$, OR, and R, in which R represents a $C_{1-12}$ achiral alkyl, or $C_{4-12}$ achiral alkenyl group, with the double bond at position 3- or higher, or hydrogen.

12. A compound according to claim 1, in which the polymerisable mesogenic residues $G^1$ and $G^2$ are each independently represented by the group of formula III

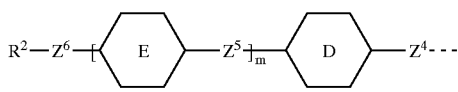

wherein
D and E are independently selected from the group consisting of optionally substituted 1,4-phenylene, pyridine-2,5-diyl, pyrimidine-2,5-diyl, trans-1,4-cyclohexylene and trans-1,3-dioxane-2,5-diyl;
m is 1 or 0,
$Z^4$ and $Z^5$ are independently selected from the group consisting a single bond, —COO—, —OOC—, —CH$_2$—CH$_2$—, —CH$_2$O—, —OCH$_2$—, —CH=CH—, —C≡C—, —(CH$_2$)$_4$— and —(CH$_2$)$_3$O—;
$Z^6$ represents a group of formula —(CH$_2$)$_p$X— in which p is an integer having a value of 1 to 18 and X is as defined in claim 1, and in which one or two non adjacent —CH$_2$— groups may be optionally replaced by —CH=CH— or in which one or two —CH$_2$— groups may be replaced by one or two additional linking groups X with the proviso that firstly the group $Z^6$ does not contain two adjacent heteroatoms and secondly when X is —CH$_2$, p can also have a value of 0
$R^2$ represents a polymerisable group selected from the group consisting of CH$_2$=C(Ph)—, CH$_2$=CW—COO—, CH$_2$=CH—COO—Ph—, CH$_2$=CW—CO—NH—, CH$_2$=CH—O—, CH$_2$=CH—OOC—, Ph—CH=CH—, CH$_2$=CH—Ph—, CH$_2$=CH—Ph—O—, $R^3$—Ph—CH=CH—COO—, $R^3$—OOC—CH=CH—Ph—O— and 2-W- epoxyethyl
in which
W represents H, Cl, Ph or a lower alkyl,
$R^3$ represents a lower alkyl with the proviso that when $R^3$ is attached to a phenylene group (—Ph—) it may also represent hydrogen or a lower alkoxy.

13. A compound according to claim 12, in which the groups D and E are independently selected from optionally substituted 1,4-phenylene and 1,4-cyclohexylene rings.

14. A compound according to claim 12, in which $Z^4$ and $Z^5$ are selected from the group consisting of a single bond, —COO—, —OOC—, —CH$_2$—CH$_2$—, —CH$_2$O—, —OCH$_2$—, —CH=CH— and —C≡C—.

15. A compound according to claim 12, in which the group $R^2$ is selected from the group consisting of CH$_2$=CW—COO— and CH$_2$=CH—O—.

16. An optical or electro-optical device comprising a compound according to claim 1.

17. A LCP network, comprising a compound according to claim 1 in cross-linked or polymerised form.

18. An optical or electro-optical device comprising a network according to claim 17.

19. A LCP mixture comprising a compound of formula (I)

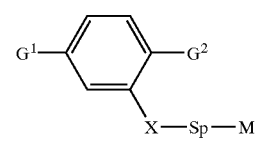

I wherein
$G^1$ and $G^2$ independently represent a polymerisable mesogenic residue;
X represents a group selected from —CH$_2$—, —O—, —CO—, —COO—, —OOC—, —CONR'—, —OCOO—, and —OCONR'—;
Sp represents a group of the formula —(CH$_2$)$_p$— in which p is an integer of 1 to 18 and in which one or two non adjacent —CH$_2$— groups are optionally replaced by —CH=CH—; or in which one or two —CH$_2$— groups are optionally replaced by one or two groups selected from the group consisting of —O—, —CO—, —COO—, —OOC—, —CONR'—, —OCOO—, and —OCONR' with the proviso that firstly the spacer group does not contain two adjacent heteroatoms and secondly when X is —CH$_2$—, p can also have a value of 0; and
M represents an achiral group of formula (II)

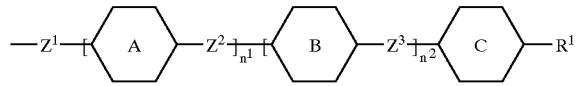

in which
A and B independently represent an optionally substituted six membered isocyclic or heterocyclic group or naphthalenediyl;
C is selected from the group consisting of an optionally substituted five and six membered isocyclic or heterocyclic group or naphthalenediyl;
$n^1$ and $n^2$ are 0 or 1 with the proviso that firstly $1 \leq n^1+n^2 \leq 2$ and secondly, when C is naphthalenediyl $0 \leq n^1+n^2 \leq 2$;
$Z^1$ is selected from the group consisting of —O—, —COO—, —OOC—, —CO—, —CONR'—, —NR'CO—, OCOO—, —OCONR'—, —NR'COO— and a single bond;

in which

R' is selected from the group consisting of hydrogen, a lower achiral alkyl group and a lower achiral alkenyl group;

$Z^2$ and $Z^3$ are independently selected from the group consisting of a single bond, —COO—, —OOC—, —CH$_2$—CH$_2$—, —CH$_2$O—, —OCH$_2$—, —CH=CH—, —C≡C—, —(CH$_2$)$_4$— and —(CH$_2$)$_3$O—; and $R^1$ is selected from the group consisting of —CN, —COR, —COOR, —OCOR, —CONR'R, —NR'COR, OCOOR, —OCONR'R, —NR'COOR, —F, Cl, —CF$_3$, —OCF$_3$, —OR and —R in which R is selected from the group consisting of hydrogen, an achiral $C_{1-18}$ alkyl and an achiral $C_{4-18}$ alkenyl group with the double bond at 3- position or higher; and R' is as defined above;

with the proviso that at most one of the rings A, B and C is a naphthalenediyl group and one or more additional suitable components.

20. A LCP network, comprising a mixture according to claim 19 in cross-linked on polymerised form.

21. An optical or electro-optical device comprising a mixture according to claim 19.

\* \* \* \* \*